United States Patent [19]

Nakada et al.

[11] Patent Number: 6,160,069

[45] Date of Patent: Dec. 12, 2000

[54] LIQUID FOR CONTACT LENSES

[75] Inventors: Kazuhiko Nakada; Tetsuji Kawai, both of Kasugai, Japan

[73] Assignee: Menicon, Co., Ltd., Aichi-ken, Japan

[21] Appl. No.: 09/271,338

[22] Filed: Mar. 18, 1999

[30] Foreign Application Priority Data

Mar. 25, 1998 [JP] Japan ................................. 10-077230

[51] Int. Cl.$^7$ ............................ C08F 12/28; C08L 39/00; G02B 3/00
[52] U.S. Cl. ........................ 526/310; 523/105; 523/106; 523/122; 524/555; 524/812
[58] Field of Search .................................... 523/105, 106, 523/122; 524/555, 812; 526/310

[56] References Cited

U.S. PATENT DOCUMENTS 5,260,385   11/1993   Iio .

FOREIGN PATENT DOCUMENTS 0 757 095     2/1997   European Pat. Off. .
10-319358    12/1998   Japan .

Primary Examiner—Peter A. Szekely
Attorney, Agent, or Firm—Browdy and Neimark

[57] ABSTRACT

A liquid for contact lenses, containing at least one of a polymer (A) having a recurring unit (a) represented by the formula (I):

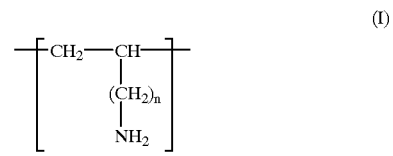

wherein n is 0 or 1 and a recurring unit (b) represented by the formula (II):

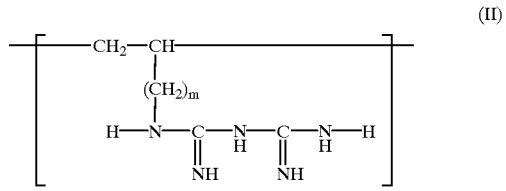

wherein m is 0 or 1, and a salt of the polymer (A). The liquid for contact lenses can extremely decrease variation of base curve of a contact lens during preservation and shipping, and shows excellent antiseptic effect and excellent antibacterial effect.

7 Claims, No Drawings

LIQUID FOR CONTACT LENSES

BACKGROUND OF THE INVENTION

The present invention relates to a liquid for contact lenses. More particularly, the present invention relates to a liquid for contact lenses, which can be preferably used for preservation, shipping, cleaning and disinfection of contact lenses.

In general, most of contact lenses, in particular, oxygen permeable hard contact lenses are prepared by using a silicone component. Accordingly, the lens surface becomes hydrophobic and wettability of the lens at initial wearing is poor. As a result, there easily occur that wearing sensation is lowered and sight cannot be sufficiently recovered.

Therefore, in order to keep surface wettability from production to wearing by users, the above oxygen permeable hard contact lens is preserved with wetting and shipped by subjection to surface treatment or immersion in a shipping solution such as physiological sodium chloride solution.

However, in the case that a contact lens is preserved with wetting and shipped in such physiological sodium chloride solution, base curve which is one of important standards of a contact lens sometimes varies.

Possibly, the above base curve of a contact lens varies during preservation of the contact lens by users.

For instance, bacteria may propagate in a preserving solution during preservation of a contact lens, or in a shipping solution during shipping of a contact lens. Accordingly, in order to prevent bacteria from propagating, an antiseptic is added to the preserving solution or the shipping solution.

However, antiseptic effect of the antiseptic is insufficient, or some of the antiseptics are poor in safety and durability. Accordingly, the antiseptic is not effective for preventing the propagation of bacteria.

In particular, in the case that a soft contact lens is immersed in the above preserving solution or the above shipping solution, which contains an antiseptic, the antiseptic sometimes adheres to the surface of the soft contact lens or is sometimes captured in the inside of the lens. Accordingly, it is desired that there is developed a method comprising using a polymerized antiseptic.

An object of the present invention is to provide a liquid for contact lenses, which can extremely decrease variation of base curve of a contact lens, in particular, an oxygen permeable hard contact lens during preservation and shipping, and which shows excellent antiseptic effect, excellent antibacterial effect and durability of these effects.

This and other objects of the present invention will become apparent from the description hereinafter.

SUMMARY OF THE INVENTION

In accordance with the present invention, there is provided a liquid for contact lenses, containing at least one of a polymer (A) having a recurring unit (a) represented by the formula (I):

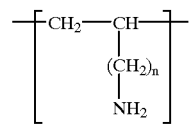

wherein n is 0 or 1 and a recurring unit (b) represented by the formula (II):

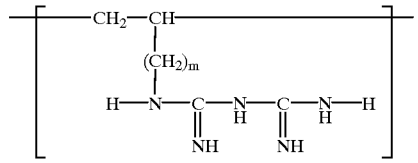

wherein m is 0 or 1, and a salt of the polymer (A).

The liquid for contact lenses of the present invention is excellent in solubility and appearance, gives little bad smell, and shows stability of antiseptic effect and antibacterial effect for a long period of time. Therefore, when a contact lens, in particular, an oxygen permeable hard contact lens is preserved and shipped in the liquid for contact lenses of the present invention, variation of base curve which is one of important standards of a contact lens can be extremely decreased.

DETAILED DESCRIPTION

The liquid for contact lenses of the present invention contains at least one of a polymer (A) having a recurring unit (a) (hereinafter referred to as "amine unit (a)" represented by the formula (I):

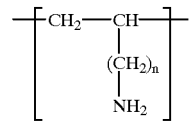

wherein n is 0 or 1 and a recurring unit (b) (hereinafter referred to as "substituted amine unit (b)") represented by the formula (II):

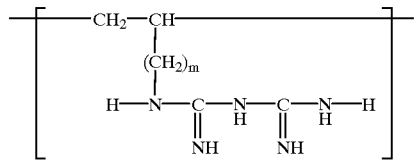

wherein m is 0 or 1, and a salt of the polymer (A). Hereinafter, at least one of the polymer (A) and the salt of the polymer (A) is referred to as "compound (A)".

In the liquid for contact lenses, the above compound (A) is an effective ingredient for decreasing variation of base curve of a contact lens during preservation and shipping, and further imparting antiseptic effect and antibacterial effect. The compound (A) can be prepared by polymerizing a monomer mixture containing at least vinylamine or allylamine which constitutes the amine unit (a) and a substituted vinylamine or a substituted allylamine which constitutes the substituted amine unit (b).

In order to more stabilize base curve of a contact lens, it is desired that the molar ratio of the amine unit (a) to the substituted amine unit (b) (amine unit (a)/substituted amine unit (b)) in the polymer (A) is at least 25/75, preferably at least 30/70. In order to impart more excellent antiseptic effect and antibacterial effect, it is desired that the molar ratio is at most 99/1, preferably at most 90/10.

In the present invention, because variation of base curve of a contact lens can be more extremely decreased and antiseptic effect and antibacterial effect can be greatly exhibited, a polymer having a recurring unit represented by the formula:

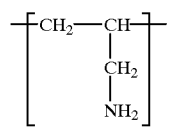

and a recurring unit represented by the formula:

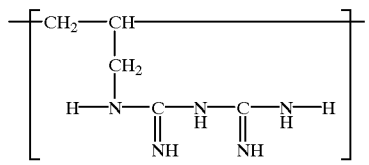

and a salt thereof are preferably used.

In order to sufficiently exhibit stability of base curve of a contact lens and sufficiently exhibit antiseptic effect and antibacterial effect, the polymer (A) or the salt thereof needs certain molecular weight. Accordingly, it is desired that weight average molecular weight of the polymer (A) or the salt thereof is at least about 1000, preferably at least about 2000. In order to remove fears that solubility of the polymer (A) or the salt thereof in medium such as water is lowered, that a uniform liquid for contact lenses cannot be easily prepared, and that handling of the polymer (A) or the salt thereof is lowered due to increase of viscosity, it is desired that weight average molecular weight of the polymer (A) or the salt thereof is at most about 200000, preferably at most about 100000.

As far as the objects of the present invention are not hindered, the polymer (A) can contain, for instance, the following recurring units and recurring units derived from the following polymerizable monomers, in addition to the amine unit (a) and the substituted amine unit (b).

Examples of a recurring unit which can be contained in the polymer (A) are, for instance, a unit showing antibacterial effect, such as a recurring unit represented by the formula (III):

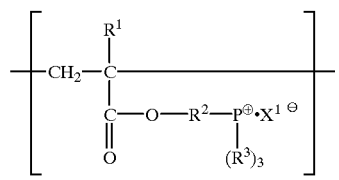

wherein $R^1$ is hydrogen atom or methyl group, $R^2$ is an alkylene group having 1 to 8 carbon atoms, $R^3$ is an alkyl group having 1 to 18 carbon atoms, and $X^1$ is a halogen atom; or a recurring unit represented by the formula (IV):

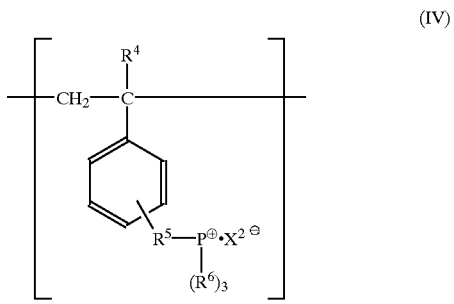

wherein $R^4$ is hydrogen atom or methyl group, $R^5$ is an alkylene group having 1 to 8 carbon atoms, $R^6$ is an alkyl group having 1 to 18 carbon atoms, and $X^2$ is a halogen atom; and the like.

The recurring unit represented by the formula (III) is derived from a compound represented by the formula (V):

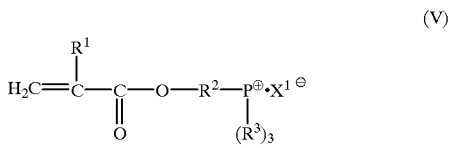

wherein $R^1$, $R^2$, $R^3$ and $X^1$ are respectively the same as the above. The recurring unit represented by the formula (IV) is derived from a compound represented by the formula (VI):

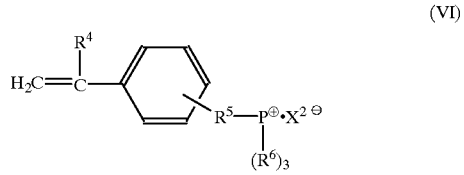

wherein $R^4$, $R^5$, $R^6$ and $X^2$ are respectively the same as the above.

In the formulas (III) and (V), $X^1$ shows a halogen atom, and in the formulas (IV) and (VI), $X^2$ also shows a halogen atom. Examples of the halogen atom are, for instance, chlorine atom, bromine atom, iodine atom and the like.

Concrete examples of the compound represented by the formula (V) are, for instance, tri-n-butyl(2-(meth)acryloyloxyethyl)phosphonium chloride, tri-n-hexyl(2-(meth)acryloyloxyethyl)phosphonium chloride, tri-n-octyl(2-(meth)acryloyloxyethyl)phosphonium chloride, tri-n-butyl(2-(meth)acryloyloxyethyl)phosphonium bromide, tri-n-hexyl(2-(meth)acryloyloxyethyl)phosphonium bromide, tri-n-octyl(2-(meth)acryloyloxyethyl)phosphonium bromide, tri-n-butyl(2-(meth)acryloyloxyethyl) phosphonium iodide, tri-n-hexyl(2-(meth)acryloyloxyethyl) phosphonium iodide, tri-n-octyl(2-(meth)acryloyloxyethyl) phosphonium iodide and the like.

Concrete examples of the compound represented by the formula (VI) are, for instance, tri-n-butyl(4-vinylbenzyl) phosphonium chloride, tri-n-hexyl(4-vinylbenzyl) phosphonium chloride, tri-n-octyl(4-vinylbenzyl) phosphonium chloride, tri-n-butyl(4 -vinylbenzyl) phosphonium bromide, tri-n-hexyl(4-vinylbenzyl) phosphonium bromide, tri-n-octyl(4-vinylbenzyl)

phosphonium bromide, tri-n-butyl(4-vinylbenzyl) phosphonium iodide, tri-n-hexyl(4-vinylbenzyl) phosphonium iodide, tri-n-octyl(4-vinylbenzyl) phosphonium iodide and the like.

It is desired that the total amount of the recurring unit represented by the formula (III) and the recurring unit represented by the formula (IV) in the polymer (A) is at most about 10 moles based on 100 moles of the total amount of the amine unit (a) and the substituted amine unit (b).

Typical examples of a polymerizable monomer constituting a recurring unit which can be contained in the polymer (A) are, for instance, a linear, branched or cyclic alkyl (meth)acrylate such as methyl (meth)acrylate, ethyl (meth)acrylate, isopropyl (meth)acrylate, n-propyl (meth)acrylate, isobutyl (meth)acrylate, n-butyl (meth)acrylate, t-butyl (meth)acrylate, 2-ethylhexyl (meth)acrylate, n-octyl (meth) acrylate, n-decyl (meth)acrylate, n-dodecyl (meth)acrylate, n-pentyl (meth)acrylate, t-pentyl (meth)acrylate, hexyl (meth)acrylate, heptyl (meth)acrylate, nonyl (meth)acrylate, stearyl (meth)acrylate, cyclopentyl (meth)acrylate or cyclohexyl (meth)acrylate; styrene; α-methylstyrene; an alkylstyrene such as methylstyrene, ethylstyrene, propylstyrene, n-butylstyrene, t-butylstyrene, isobutylstyrene or pentylstyrene; an alkyl-α-methylstyrene such as methyl-α-methylstyrene, ethyl-α-methylstyrene, propyl-α-methylstyrene, n-butyl-α-methylstyrene, t-butyl-α-methylstyrene, isobutyl-α-methylstyrene or pentyl-α-methylstyrene; and the like.

It is desired that the amount of the recurring unit derived from the above polymerizable monomer in the polymer (A) is at most about 10 moles based on 100 moles of the total amount of the amine unit (a) and the substituted amine unit (b).

In the present invention, a polymerization initiator is added to the desired amount of the monomer mixture containing vinylamine or allylamine and the substituted vinylamine or the substituted allylamine, and as occasion demands, the compound represented by the formula (V), the compound represented by the formula (VI) and the polymerizable monomer, and then, they are polymerized by a usual method to give a polymer (A).

In order to polymerize the monomer mixture, usual polymerization methods can be employed. For instance, after the polymerization initiator is added to the monomer mixture to give a mixture, the mixture is gradually heated within the range of room temperature to, for instance, in case of using a solvent, boiling point of the solvent, or the mixture is irradiated with electromagnetic wave such as microwave, ultraviolet ray or radiation (γ ray). During the thermal polymerization, the temperature of the mixture may be raised stepwise. The polymerization may be carried out by a bulk polymerization method, a solution polymerization method using a solvent such as tetrahydrofuran, alcohols, toluene or dimethylformamide, or the other polymerization methods.

Typical examples of a thermal polymerization initiator are, for instance, azobisisobutyronitrile, azobisdimethylvaleronitrile, benzoyl peroxide, t-butyl hydroperoxide, cumene hydroperoxide and the like. These can be used alone or in admixture thereof. In the case that the polymerization is carried out utilizing electromagnetic wave, it is desired that a photopolymerization initiator and a polymerization sensitizer are further added to the above mixture. It is desired that the amount of the polymerization initiators and the polymerization sensitizer is about 0.001 to 2 parts by weight (hereinafter referred to as "part(s)"), preferably about 0.01 to 1 part based on 100 parts of the total amount of the monomer mixture.

After the thus obtained polymer (A) is washed with water, methanol or a mixture solution thereof, the polymer (A) is purified by deairing and drying.

The amount of each component contained in the monomer mixture, which is used for preparation of the polymer (A) is suitably adjusted in consideration of the kinds and the amount of recurring units to be included in the polymer (A). For instance, it is desired that the amount of vinylamine or allylamine and the substituted vinylamine or the substituted allylamine in the monomer mixture is suitably adjusted so that the molar ratio of the total amount of the amine unit (a) and the substituted amine unit (b) to the total amount of the other units is within the above range and so that the molar ratio of the amine unit (a) to the substituted amine unit (b) is within the above range. Usually, it is desired that the monomer mixture contains about 1 to 99% by weight of vinylamine or allylamine and about 1 to 99% by weight of the substituted vinylamine or the substituted allylamine. It is desired that the total amount of the compound represented by the formula (V), the compound represented by the formula (VI) and the polymerizable monomer is suitably adjusted according to the amount of vinylamine or allylamine and the substituted vinylamine or the substituted allylamine, and the total amount of the monomer mixture reaches 100% by weight.

In the present invention, in addition to the polymer (A), the salt of the polymer (A) can be also used.

Typical examples of the salt of the polymer (A) are, for instance, hydrochloride of the polymer (A), acetate of the polymer (A) and the like.

Various polymers (A) and salts thereof can be used alone or in admixture thereof.

In order to sufficiently decrease variation of base curve of a contact lens during preservation and shipping, and further sufficiently exhibit antiseptic effect and antibacterial effect, it is desired that the content of the compound (A) in the liquid for contact lenses is at least 0.01 w/v %, preferably at least 0.1 w/v %. In order to remove a fear that a contact lens is easily stained during dry and handling is lowered because viscosity of the liquid for contact lenses is too increased, it is desired that the content of the compound (A) in the liquid for contact lenses is at most 10 w/v %, preferably at most 3 w/v %.

The liquid for contact lenses can contain, for instance, an antiseptic, a chelating agent and the like in addition to the above compound (A).

The above antiseptic is a component for preventing contamination for the liquid for contact lenses with germs and preventing contamination for a contact lens with bacteria during preservation and shipping in the liquid for contact lenses. By using the antiseptic, antiseptic effect and antibacterial effect which are exhibited from the compound (A) can be more improved.

The antiseptic is an ophthalmic physiologically acceptable component and is not particularly limited. Typical examples of the antiseptic are, for instance, a mercury antiseptic such as mercury phenyl nitrate, mercury phenyl acetate or thimerosal; a surface active agent type antiseptic such as benzalkonium chloride or pyridinium bromide; an alcohol antiseptic such as chlorhexidine, polyhexamethylene biguanide or chlorobutanol; methylparaben, propylparaben, dimethyloldimethylhydantoin, imidazoliumurea; and the like. These can be used alone or in admixture thereof.

In order to sufficiently exhibit further antiseptic effect, it is desired that the content of the antiseptic in the liquid for contact lenses is at least 0.00001 w/v %, preferably at least 0.00003 w/v %. When the content of the antiseptic in the liquid for contact lenses is too large, there are tendencies that the antiseptic directly inserts into eyes, so eyes are injured and that some of the antiseptics impart bad influence to standards and properties of a contact lens. Accordingly, it is desired that the content of the antiseptic in the liquid for contact lenses is at most 0.5 w/v %, preferably at most 0.3 w/v %.

The above chelating agent is a component for preventing calcium, which is included in the liquid for contact lenses or lacrimal fluid adhering a contact lens, from accumulating on a contact lens.

The chelating agent is an ophthalmic physiologically acceptable component and is not particularly limited. Typical examples of the chelating agent are, for instance, ethylenediaminetetraacetic acid, sodium ethylenediaminetetraacetate, phytic acid, citric acid and the like. These can be used alone or in admixture thereof.

In order to sufficiently exhibit effect of preventing accumulation of calcium on a contact lens, it is desired that the content of the chelating agent in the liquid for contact lenses is at least 0.001 mol/l, preferably at least 0.0015 mol/l. When the content of the chelating agent in the liquid for contact lenses is too large, there is a tendency that effects are not very improved for considering the content, so economy is lowered. Accordingly, it is desired that the content of the chelating agent in the liquid for contact lenses is at most 0.1 mol/l, preferably at most 0.05 mol/l.

The liquid for contact lenses can contain, for instance, additives such as a buffer, an isotonizing agent, a thickener and a surface active agent in addition to the antiseptic and the chelating agent.

The above buffer is a component for setting pH of the liquid for contact lenses within the range of about 5 to 9 near to pH of lacrimal fluid, preventing variation of pH of the liquid for contact lenses, due to outside cause, and protecting shape and optical property of a contact lens during preservation and shipping.

The buffer is an ophthalmic physiologically acceptable component and is not particularly limited. Typical examples of the buffer are, for instance, boric acid, sodium borate, phosphoric acid, sodium phosphate, citric acid, sodium citrate, lactic acid, sodium lactate, glycine, an amino acid such as glutamic acid, sodium salt of an amino acid, malic acid, sodium malate and the like. These can be used alone or in admixture thereof.

In order to sufficiently exhibit buffer effect, it is desired that the content of the buffer in the liquid for contact lenses is at least 0.005 mol/l, preferably at least 0.01 mol/l. When the content of the buffer in the liquid for contact lenses is too large, there is a tendency that buffer effect is not very improved and osmotic pressure is heightened, so bad influence is imparted to shape of a contact lens. Accordingly, it is desired that the content of the buffer in the liquid for contact lenses is at most 0.5 mol/l, preferably at most 0.15 mol/l.

The above isotonizing agent is a component for setting osmotic pressure of the liquid for contact lenses within the range of 280 to 320 mOs/kg near to osmotic pressure of lacrimal fluid, and supporting maintenance of shape of a contact lens during preservation and shipping.

The isotonizing agent is an ophthalmic physiologically acceptable component and is not particularly limited. Typical examples of the isotonizing agent are, for instance, an inorganic salt such as sodium chloride, potassium chloride or calcium chloride; compounds which are exemplified as the above buffer; and the like. These can be used alone or in admixture thereof.

In order to sufficiently impart osmotic pressure to the liquid for contact lenses, it is desired that the content of the isotonizing agent in the liquid for contact lenses is at least 0.01 mol/l, preferably at least 0.05 mol/l. When the content of the isotonizing agent in the liquid for contact lenses is too large, there is a tendency that osmotic pressure is heightened, so bad influence is imparted to shape of a contact lens. Accordingly, it is desired that the content of the isotonizing agent in the liquid for contact lenses is at most 0.5 mol/l, preferably at most 0.15 mol/l.

The above thickener is a component for protecting a contact lens from outside stress during preservation and shipping.

The thickener is an ophthalmic physiologically acceptable component and is not particularly limited. Typical examples of the thickener are, for instance, a viscous substance such as polyvinyl alcohol, poly-N-vinylpyrrolidone, polyacrylamide, hydrolyzate of polyacrylamide, polyacrylic acid, xanthane gum, hydroxyethylcellulose, carboxymethylcellulose, methylhydroxyethylcellulose, methylhydroxypropylcellulose, methylcellulose, sodium alginate, polyethylene glycol, gelatin, sodium chondroitin sulfate or gum arabic; and the like. These can be used alone or in admixture thereof.

In order to sufficiently protect a contact lens from outside stress during preservation and shipping, it is desired that the content of the thickener in the liquid for contact lenses is at least 0.01 w/v %, preferably at least 0.02 w/v %. When the content of the thickener in the liquid for contact lenses is too large, there is a tendency that the liquid for contact lenses is gelated, so preservative property and shipping property are lowered. Accordingly, it is desired that the content of the thickener in the liquid for contact lenses is at most 10 w/v %, preferably at most 5 w/v %.

The above surface active agent is a component for more improving cleaning effect of the liquid for contact lenses.

The surface active agent is an ophthalmic physiologically acceptable component and is not particularly limited. Various surface active agents such as an anionic surface active agent, a nonionic surface active agent and a combination of anionic surface active agent with nonionic surface active agent can be used.

Typical examples of the anionic surface active agent are, for instance, sodium alkylsulfate, sodium alkylbenzenesulfonate, sodium alkyloylmethyltaurinate, sodium alkyloylsarcosinate, sodium α-olefinsulfonate, sodium polyoxyethylene alkyl ether phosphate, sodium polyoxyethylene alkyl ether sulfate, sodium polyoxyethylene alkyl phenyl ether sulfate, sodium di(polyoxyethylene alkyl ether) phosphate and the like. These can be used alone or in admixture thereof. Among them, sodium alkylsulfate, sodium alkylbenzenesulfonate, sodium α-olefinsulfonate, sodium polyoxyethylene alkyl ether sulfate and sodium polyoxyethylene alkyl phenyl ether sulfate show excellent cleaning effect, and are preferable. When these anionic surface active agents are used with the nonionic surface active agent, effective cleaning effect is exhibited during immersion and preservation for a short period of time.

In order to sufficiently exhibit cleaning effect, it is desired that the content of the anionic surface active agent in the liquid for contact lenses is at least 0.01 w/v %, preferably at least 0.02 w/v %. When the content of the anionic surface active agent in the liquid for contact lenses is too large, there is a tendency that cleaning effect is not very improved and hands become rough. Accordingly, it is desired that the content of the anionic surface active agent in the liquid for contact lenses is at most 10 w/v %, preferably at most 5 w/v %.

Typical examples of the nonionic surface active agent are, for instance, an adduct of higher alkylamine with polyethylene glycol, an adduct of higher fattyamide with polyethylene glycol, an ester of polyglycerin with higher fatty acid, an ester of polyalkylene glycol such as polyethylene glycol with higher fatty acid, a polyethylene glycol copolymer ester, an ester of adduct (of polyvalent alcohol with polyethylene glycol) with higher fatty acid, an ether of polyethylene glycol with higher alcohol, an ether of polyglycerin with higher alcohol, an ether of polyethylene glycol with alkylphenol, a condensate of ether (of polyethylene glycol with alkylenephenol) with formaldehyde, a polypropylene glycol-polyethylene glycol copolymer, a phosphate, castor oil, hydrogenated castor oil, a sorbitan alkylester of polyethylene glycol, an adduct of sterol with polyethylene glycol and the like. These can be used alone or in admixture thereof. Among them, an ether of polyethylene glycol with higher alcohol, an ester of polyethylene glycol with higher fatty acid, an ester of polyglycerin with higher fatty acid, an ether of polyethylene glycol with alkylphenol and a sorbitan alkylester of polyethylene glycol show excellent cleaning effect, and are preferable.

In order to sufficiently exhibit cleaning effect, it is desired that the content of the nonionic surface active agent in the liquid for contact lenses is at least 0.01 w/v %, preferably at least 0.02 w/v %. When the content of the nonionic surface active agent in the liquid for contact lenses is too large, there is a tendency that cleaning effect is not very improved and hands become rough. Accordingly, it is desired that the content of the nonionic surface active agent in the liquid for contact lenses is at most 10 w/v %, preferably at most 5 w/v %.

When the anionic surface active agent and the nonionic surface active agent are used at the same time, it is desired that the content of the anionic surface active agent and the content of the nonionic surface active agent are within the above defined range, respectively. Also, it is desired that the total amount of the anionic surface active agent and the nonionic surface active agent in the liquid for contact lenses is 0.02 to 20 w/v %, preferably 0.05 to 10 w/v %.

The liquid for contact lenses of the present invention contains the compound (A) as an effective ingredient and, as occasion demands, contains the antiseptic, the chelating agent and the other additives. As a medium, water such as distilled water or purified water may be contained in the liquid for contact lenses. The amount of an aqueous medium such as water is adjusted so that the total amount of the liquid for contact lenses reaches 100%.

For instance, the compound (A) is added to the prescribed amount of the aqueous medium and, as occasion demands, the additives such as antiseptic, chelating agent, buffer, isotonizing agent, thickener and surface active agent are added thereto. These are sufficiently mixed and stirred with each other, and the compound (A) and the additives are dissolved in the aqueous medium to give a solution. Then, the solution is filtrated to give the liquid for contact lenses of the present invention.

Viscosity of the liquid for contact lenses is not particularly limited. In consideration of handling during preservation and shipping of a contact lens, it is preferable that viscosity of the liquid for contact lenses is at most about 200 cP at 25° C.

It is preferable that pH of the liquid for contact lenses is 5 to 9, which is much the same as pH of lacrimal fluid.

In the case that various contact lenses are immersed in the thus obtained liquid for contact lenses of the present invention, the various contact lenses can be preserved and shipped with hardly varying base curve thereof. In addition, contamination for the liquid for contact lenses itself with bacteria can be prevented and various contact lenses can be cleaned or disinfected in the liquid for contact lenses.

The liquid for contact lenses of the present invention can be suitably used as a preserving solution, a shipping solution, a cleaning solution, a disinfecting solution or a liquid used for at least two of preservation, shipping, cleaning and disinfection.

A contact lens can be preserved, shipped, cleaned or disinfected by entirely immersing itself in the liquid for contact lenses in the prescribed vessel and sealing up the vessel.

A contact lens which is preserved, shipped, cleaned or disinfected in the liquid for contact lenses is not particularly limited. Various contact lenses such as a water-absorptive contact lens and a non-water-absorptive contact lens and be applied. Also, various contact lenses such as a soft contact lens and a hard contact lens can be applied. Even if an oxygen permeable hard contact lens prepared by polymerizing a monomer mixture containing silicone compounds such as a siloxanyl (meth)acrylate monomer, a siloxanyl-styrene monomer, a siloxanyl fumarate and a siloxanyl itaconate is immersed in the liquid for contact lenses, variation of base curve of the oxygen permeable hard contact lens can be extremely decreased during preservation and shipping.

The liquid for contact lenses of the present invention is more specifically described and explained by means of the following Examples. It is to be understood that the present invention is not limited to the Examples, and various changes and modifications may be made in the invention without departing from the spirit and scope thereof.

REFERENCE EXAMPLE 1

Synthesis of Polyallylamine Biguanide (1) Synthesis of guanyl-O-methylisourea hydrochloride In a flask, 21.0 g (0.25 mole) of dicyandiamide (made by Nacalai tesque Co., Ltd., trade code: 119-31) was dissolved in 2000 ml of anhydrous methanol, and 50 ml of methanolic hydrochloric acid solution having a concentration of 5 mol/l (the amount of hydrogen chloride: 0.25 mole) was added thereto. Then, the flask was sealed up and sufficiently shaken, and the reaction solution in the flask was allowed to stand at room temperature for 50 hours.

Then, after the reaction solution in the flask was concentrated to about 100 ml by reducing the pressure at 40° C. in a water bath, 60 ml of anhydrous ethanol was added thereto. A reflex condenser was attached to the flask, and the concentrated reaction solution in the flask was dissolved in anhydrous ethanol with boiling in the water bath. Then, a little amount of impurity was filtrated and removed from the reaction solution to give a filtrate.

After the obtained filtrate in a vessel was allowed to stand all through the night, a crystal was precipitated and the crystal was separated from mother liquor by tipping the vessel. The crystal was washed with anhydrous ethanol and ethyl ether for one time, respectively, and dried at 60° C. in a drier to give 7.4 g of a light yellow crystal. The yield was 19%.

Furthermore, the synthesis was carried out again in the same manner and condition as the above to give 8.2 g of a light yellow crystal. The yield was 22%.

Melting point of the obtained light yellow crystals was 158° C. Elemental analysis of the light yellow crystals was carried out. The result is shown below.

| [Elemental analysis (C₃H₉ON₄Cl)] | | | | |
|---|---|---|---|---|
| | C | H | N | Cl |
| Theoretical value (%) | 23.61 | 5.95 | 36.72 | 23.24 |
| Analyzed value (%) | 24.16 | 6.03 | 36.45 | 23.38 |

From the above results, it was recognized that the obtained light yellow crystals were the aimed guanyl-O-methylisourea hydrochlorides.

(2) Synthesis of Polyallylamine Biguanide

In an atmosphere of nitrogen gas, 11.0 g of polyallylamine (made by Nitto Boseki Co., Ltd., trade name: PAA-HCl-3S) (the amount of allylamine unit: 0.11 mole) was dissolved in 2.53 g of an equimolar sodium solution (100 ml of methanol solution containing 0.11 mole of sodium) to give a solution. The solution was stirred at 45° C. for 4 hours, and the precipitated NaCl was filtrated and removed from the solution to give a filtrate.

Then, 15.45 g (0.10 mole) of guanyl-O-methylisourea hydrochloride obtained in the above step (1) was dissolved in the above filtrate, and they were stirred at 35° C. for 26 hours in an atmosphere of nitrogen gas to give a solution. After 26 hours, pH of the solution was adjusted to 4 by using dilute hydrochloric acid, so that the reaction was stopped.

The obtained reaction product was reprecipitated in acetone to give a polymer. After the polymer was dissolved in a little amount of distilled water, the polymer was reprecipitated and purified in acetone and further, dried under vacuum to give 8.03 g of a purified polymer. The yield was 45%.

Infrared absorption spectrum of the obtained purified polymer was examined. As a result, peaks of absorption derived from biguanide were shown at 1640 $cm^{-1}$ and 1546 $cm^{-1}$. Elemental analysis of the purified polymer was carried out. The result is shown below.

| [Elemental analysis (C₃H₈NCl:C₅H₁₂N₅Cl:acetone = 4:6:3)] | | | | |
|---|---|---|---|---|
| | C | H | N | Cl |
| Theoretical value (%) | 37.95 | 7.62 | 29.50 | 21.96 |
| Analyzed value (%) | 35.21 | 7.66 | 28.90 | 21.39 |

From the above results, it was recognized that the obtained purified polymer was the aimed polyallylamine biguanide (polymer (A)). Structure and property of the polyallylamine biguanide are shown in Table 1.

REFERENCE EXAMPLE 2

Synthesis of Polyallylamine Biguanide (1) Synthesis of guanyl-O-methylisourea hydrochloride The aimed guanyl-O-methylisourea hydrochloride was obtained in the same manner as in Reference Example 1.

(2) Synthesis of polyallylamine biguanide

In the same manner as in Reference Example 1 except that the reaction time during reaction of the filtrate obtained by dissolving the polyallylamine in the sodium solution with the guanyl-O-methylisourea hydrochloride was changed from 26 hours to 5 hours, 6.4 g of a purified polymer was prepared. The yield was 36%.

Infrared absorption spectrum of the obtained purified polymer was examined. As a result, peaks of absorption derived from biguanide were shown at 1640 $cm^{-1}$ and 1546 $cm^{-1}$. Elemental analysis of the purified polymer was carried out. The result is shown below.

| [Elemental analysis (C₃H₈NCl:C₅H₁₂N₅Cl:acetone = 7:3:3)] | | | | |
|---|---|---|---|---|
| | C | H | N | Cl |
| Theoretical value (%) | 39.67 | 8.16 | 22.63 | 26.02 |
| Analyzed value (%) | 39.02 | 8.20 | 22.28 | 25.77 |

From the above results, it was recognized that the obtained purified polymer was the aimed polyallylamine biguanide (polymer (A)). Structure and property of the polyallylamine biguanide are shown in Table 1.

EXAMPLES 1 to 2

Polymer (A) shown in Table 1 was added to distilled water. They were stirred at room temperature or with slightly heating for about 60 minutes to dissolve the polymer (A) in distilled water. The obtained solution was filtrated to give 300 ml of a liquid for contact lenses, containing 1 w/v % of the polymer (A).

Solubility, appearance, bad smell, pH, viscosity and, antiseptic and antibacterial property of the liquid for contact lenses were examined according to the following methods. The results are shown in Table 2.

(i) Solubility

Existence of insoluble components in the liquid for contact lenses was examined with naked eyes and evaluated according to the following criteria for evaluation.

Criteria for Evaluation

A: There are no insoluble components at all.
B: There is a slight insoluble component.
C: There are remarkably many insoluble components.

(ii) Appearance

Appearance of the liquid for contact lenses was observed with naked eyes and evaluated according to the following criteria for evaluation.

Criteria for Evaluation

A: The liquid is uniform and transparent.
B: The liquid is slightly cloudy in white.
C: The liquid is remarkably cloudy in white.

(iii) Bad Smell

Existence of bad smell of the liquid for contact lenses was examined at a distance of 5 cm and evaluated according to the following criteria for evaluation.

Criteria for Evaluation

A: Bad smell is not felt at all.
B: Bad smell is slightly felt.
C: Bad smell is remarkably felt.

(iv) pH

Using glass electrode type pH meter (HORIBA pH METER F-13 made by Horibaseisakusho Co., Ltd.), pH of the liquid for contact lenses was measured at 25° C.

(v) Viscosity

Using B type viscosimeter, viscosity (cP) of the liquid for contact lenses was measured at 25° C.

(vi) Antiseptic and Antibacterial Property

According to United States Pharmacopoeia, the following antiseptic effect test was carried out by organism challenge test, and antiseptic and antibacterial property of the liquid for contact lenses was examined.

Into the liquid for contact lenses was inoculated $1.0 \times 10^5$ (Example 1) or $9.0 \times 10^5$ (Example 2) Gram-positive vegetative bacteria (Staphylococcus aureus). Then, the liquid for contact lenses was allowed to stand at 37° C. for 24 hours. After 24 hours, the number of bacteria in the liquid for contact lenses was measured.

Then, a monomer mixture of 50 parts of siloxanyl methacrylate, 40 parts of trifluoroethyl methacrylate, 10 parts of methyl methacrylate and 5 parts of ethylene glycol dimethacrylate was copolymerized to give a polymer. The polymer was molded to give an oxygen permeable hard contact lens having a thickness of 0.12 mm.

Each base curve of two sets of five oxygen permeable hard contact lenses was previously measured. Then, the average base curve of the above five contact lenses before maintenance was calculated.

The above two sets of five oxygen permeable hard contact lenses were respectively put in a case for contact lenses, and the liquid for contact lenses in Example 1 or the liquid for contact lenses in Example 2 was put in each case. The five oxygen permeable hard contact lenses were immersed in each liquid for contact lenses, and the case was sealed up and maintained as it were at 40° C. After 2 weeks and 4 weeks, each base curve of the five oxygen permeable hard contact lenses was measured.

According to the difference between base curve of the contact lens after maintenance and previously measured base curve of the contact lens, the variation of base curve was calculated. Then, the average variation of base curve of the five contact lenses was calculated. Using the average base curve of the five contact lenses before maintenance and the average variation of base curve of the five contact lenses, the variation coefficient of base curve (%) was calculated according to the following equation. The results are shown in Table 2. Variation coefficient of base curve (%)={(Average variation of base curve)/(Average base curve before maintenance)}×100.

COMPARATIVE EXAMPLE 1

The variation coefficient of base curve was calculated in the same manner as in Examples 1 to 2 except that physiological sodium chloride solution was used instead of the liquid for contact lenses in Examples 1 to 2. The results are shown in Table 2.

TABLE 1

| Example No. | Kinds of polymer (A) |
|---|---|
| 1 | Polyallylamine biguanide obtained in Reference Example 1 [Amine unit (a)/substituted amine unit (b) (molar ratio):about 40/60] [Weight average molecular weight (measured by gel permeation chromatography):about 15000] |
| 2 | Polyallylamine biguanide obtained in Reference Example 2 [Amine unit (a)/substituted amine unit (b) (molar ratio):about 70/30] [Weight average molecular weight (measured by gel permeation chromatography):about 11000] |

TABLE 2

| | Properties of liquid for contact lenses | | | | | | | |
|---|---|---|---|---|---|---|---|---|
| | | | | | | Antiseptic and antibacterial property (Number of | Variation coefficient of base curve of contact lens (%) | |
| Example No. | Solubility | Appearance | Bad smell | pH | Viscosity (cP) | bacteria after 24 hours) | After 2 weeks | After 4 weeks |
| 1 | A | A | A | 6.8 | 50≧ | $5.0 \times 10^2$ | 0.1 | 0.2 |
| 2 | A | A | A | 6.8 | 50≧ | $2.2 \times 10^3$ | 0.1 | 0.2 |
| Comparative Example | | | | | | | | |
| 1 | — | — | — | — | — | — | 0.4 | 0.8 |

From the results shown in Table 2, it can be understood that all liquids for contact lenses prepared in Examples 1 to 2 have suitable pH and viscosity, show excellent solubility and appearance, give out no bad smell at all, and are extremely excellent in antiseptic and antibacterial property.

It can be understood that when a contact lens is preserved in the liquids for contact lenses prepared in Examples 1 to 2, the variation coefficient of base curve of the contact lens is remarkably small, of course after preservation for 2 weeks, even after preservation for 4 weeks, compared with preservation in physiological sodium chloride solution in Comparative Example 1.

In addition to the ingredients used in the Examples, other ingredients can be used in the Examples as set forth in the specification to obtain substantially the same results.

What is claimed is:

1. A liquid for contact lenses, containing 0.01–10 w/v % of at least one of a polymer (A) having a recurring unit (a) represented by the formula (I):

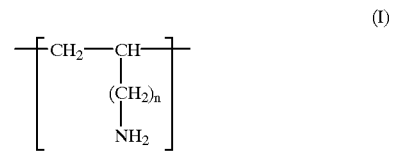

(I)

wherein n is 0 or 1 and a recurring unit (b) represented by the formula (II):

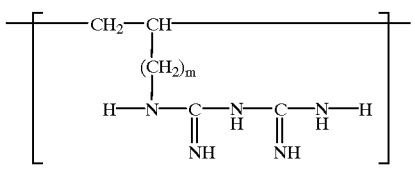

(II)

wherein m is 0 or 1, and a salt of the polymer (A).

2. The liquid for contact lenses of claim 1, wherein the polymer (A) is a polymer having a recurring unit represented by the formula:

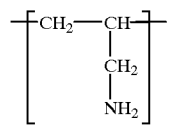

and a recurring unit represented by the formula:

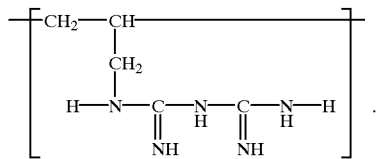

3. The liquid for contact lenses of claim 1, wherein the molar ratio of the recurring unit (a) to the recurring unit (b) (recurring unit (a)/recurring unit (b)) in the polymer (A) is 25/75 to 99/1.

4. The liquid for contact lenses of claim 1, which contains at least one of an antiseptic, a chelating agent, a buffer, an isotonizing agent, a thickener and a surface active agent.

5. The liquid for contact lenses of claim 1, which is a preserving solution, a shipping solution, a cleaning solution, a disinfecting solution or a liquid used for at least two of preservation, shipping, cleaning and disinfection.

6. The liquid for contact lenses of claim 1, wherein the content of at least one of the polymer (A) and the salt of the polymer (A) is 0.01 to 3 w/v %.

7. The liquid for contact lenses of claim 1, wherein the content of at least one of the polymer (A) and the salt of the polymer (A) is 0.1 to 3 w/v %.

* * * * *